United States Patent [19]
Schneider et al.

[11] Patent Number: 6,048,543
[45] Date of Patent: Apr. 11, 2000

[54] AMINO ACID COMPOSITIONS AND USE THEREOF IN CLINICAL NUTRITION

[75] Inventors: Heinz Schneider, Cordast, Switzerland; Ronald G. Thurman, Chapel Hill, N.C.

[73] Assignee: Novartis Nutrition AG, Berne, Switzerland

[21] Appl. No.: 08/894,570

[22] Filed: Aug. 22, 1997

Related U.S. Application Data

[63] Continuation-in-part of application No. 08/392,694, filed as application No. PCT/EP96/00739, Feb. 22, 1996, Pat. No. 5,656,608.

[30] Foreign Application Priority Data

Jun. 14, 1995 [GB] United Kingdom ............... 9512100

[51] Int. Cl.[7] .................................................. A61K 47/00
[52] U.S. Cl. ........................ 424/442; 514/42; 514/44; 514/45; 514/554; 514/663; 562/512; 562/553; 424/439
[58] Field of Search ........................... 514/42, 44, 45, 514/554, 663; 530/350; 562/512, 553; 424/439, 442

[56] References Cited

U.S. PATENT DOCUMENTS

| | | | |
|---|---|---|---|
| 4,988,724 | 1/1991 | Ajani et al. | 514/399 |
| 4,994,492 | 2/1991 | Kendall, et al. | |
| 5,198,465 | 3/1993 | Dioguardi | |
| 5,231,085 | 7/1993 | Alexander et al. | 514/44 |
| 5,260,279 | 11/1993 | Greenberg | 514/21 |
| 5,430,064 | 7/1995 | Hirsch et al. | |
| 5,462,924 | 10/1995 | Kihlberg et al. | 574/12 |
| 5,508,262 | 4/1996 | Norman, Jr. | 514/8 |
| 5,525,629 | 6/1996 | Crimmin et al. | 514/542 |
| 5,571,783 | 11/1996 | Montagne et al. | 514/2 |
| 5,576,287 | 11/1996 | Zaloga et al. | 514/2 |
| 5,576,351 | 11/1996 | Yoshimura et al. | 514/565 |
| 5,656,608 | 8/1997 | Schneider et al. | 514/42 |

FOREIGN PATENT DOCUMENTS

| | | |
|---|---|---|
| 2078712 | 3/1993 | Canada . |
| 367724 | 10/1989 | European Pat. Off. . |
| 417803 | 9/1990 | European Pat. Off. . |
| 0506965 | 10/1992 | European Pat. Off. . |
| 0614616 | 9/1994 | European Pat. Off. . |
| 2591893 | 6/1987 | France . |
| 4133366 | 10/1991 | Germany . |
| 61186320 | 2/1985 | Japan . |
| 9109524 | 12/1989 | WIPO . |
| 9204023 | 3/1992 | WIPO . |
| 9305780 | 4/1993 | WIPO . |
| 5/02398 | 7/1994 | WIPO . |
| 95/02398 | 1/1995 | WIPO . |
| 95/29675 | 11/1995 | WIPO . |
| 96/25861 | 8/1996 | WIPO . |

OTHER PUBLICATIONS

Belokrylov, et al., Byull. Eksp. Biol. Med., vol. 102, pp 931–933, (1986).
Belokrylov, et al., Int. J. Immunopharmac, vol. 14, pp. 1285–1292 (1986).
Bennett, et al., Nephrology Dialysis Transplantation, vol. 9, pp. 141–145 (1994).
Butter, et al., Transplantation Proceedings, vol. 23, No. 5, 1991, pp. 2378–2379.
Chemical Abstract JP04091032.
Chemical Abstract JP04091033.
De Nicola, et al., J Am Soc Nephrol, vol. 2 pp. 47P (1991).
De Nicola, et al., J. Clin Invest, vol. 92 pp. 1859–1865 (1993).
Derwent Abstract No. 72–27052T Oct. 15, 1970.
Derwent Abstract No. 82–02453E Jun. 30, 1980.
Derwent Abstract No. 82–55461E Nov. 19, 1980.
Derwent Abstract No. 83–07759K Jul. 3, 1981.
Derwent Abstract No. 90–141600.
Derwent Abstract No. 92–235891.
Derwent Abstract No. 93–052862.
Derwent Abstract No. 95–268841, Apr. 7, 1993.
Garza–Quintero, et al., American Physiological Society, F1075–F1082, (1990).
Hagglund, et al., Immunobiol. vol. 188, pp. 62–69 (1993).
Heyman, et al., Kidney International, vol. 42, pp. 41–45, (1992).
Ikejima, et al., American Physiological Society, G1581–G1586, (1997).
Jain, et al., Indian Journal of Experimental Biology, vol. 27, pp. 292–293 (1989).
Kulkarni, et al., Nutrition, vol. 6, pp 66–9 (1990).
Mobb GE, Renal Fail, vol. 14, pp 175–181, (1992).
Nissim, et al., Kidney International, vol. 49, pp 684–695.
Snyder, et al., J. Pharmac. 53, 473–484, (1975).
Spittler, et al., Department of Surgery.
Stryer, L., Biochemistry.
Thurman, et al., Hepatology, vol. 24, abstract No. 1230, (1996).
Thurman, et al., Transplantation, vol. 63, pp. 1661–1667, (1997).
Toth, et al., Acta Microbiol, Hung. vol. 32, pp. 369–372 (1985).
Toth, et al., Acta Microbiol. Hung. vol. 32, pp. 363–368 (1985).
Weinberg, et al., Kidney International, vol. 52, pp. 140–151, (1997).

(List continued on next page.)

*Primary Examiner*—Thurman K. Page
*Assistant Examiner*—Lakshmi Channavajjala
*Attorney, Agent, or Firm*—Hesna J. Pfeiffer; Michael P. Morris

[57] ABSTRACT

A method for treating a human having elevated tumor necrosis factor levels by administrating an effective amount of one of the amino acids glycine, alanine, or serine.

19 Claims, No Drawings

OTHER PUBLICATIONS

Yin, et al., Laboratory of Hepatobiology and Toxicology, 28 pages.

Young, et al., Kidney International, vol. 48, pp. 439–448, (1995).

Shiratori et al, Modulation of KC/GRO protein (interleukin–8 related proteins in rodents) release from hepatocytes by biologically active mediators, Biochemical and Biophysical Research Communications, vol. 203(3), 1398–1403, Sep. 30, 1994.

Remick et al, Cytokines and extrahepatic sequelae of Ischemia–Reperfusion injury to liver, Annals of New York Academy of Sciences, vol. 723, 271–283, Jun. 17, 1994.

Grimble et al, Cysteine and glycine supplemetation modulate the metabolic response to Tumor Necrosis Factor in Rats fed a low protein diet, Journal of Nutrition, 122, 2066–2073, 1992.

Fishman, M., Cytolytic activities of activated macrophage versus paraformaldehyde–fixed macrophages; soluble versus membrane–associated TNF, Cellular Immunology, 137, 164–174, 1991.

Blum, et al., Life Sciences, vol. 14, pp 557–565 (1974).

Jeevanandam, et al., The Lancet, pp. 1423–1426 (Jun. 30, 1984).

Derwent Abstract No. 93–183072/23 (1991)

Derwent Abstract No. 93–126956/16 (1991).

Derwent Abstract No. 89–286411/40 (1988).

Derwent Abstract No. 93–299541/38 (1984).

Butter, et al., Transplantation, vol. 56, pp. 817–822, No. 4, (Oct. 1993).

Weinberg, et al., American Journal of Physiology, vol. 258, pp. C1127–C1140, (1990).

Weinberg, et al., The Amer. Society for Clinical Investigation, Inc., pp. 1446–1454, vol. 80, (Nov. 1987).

Grimble, et al., J. Nutrition, vol. 122, pp. 2066–2073, (Jun. 22, 1992).

M. Schilling, et al., Transplantationsmedizin, vol. 6, pp. 140–143, (1994).

Endre, et al., Biochemical & Biophysical Res. Comm., vol. 202, No. 3, pp. 1639–1644.

Ozaki, et al., Transplantations, vol. 58, No. 6, pp. 753–755 (1994).

Pathirana et al., Journal Nutrition, No. 7, pp. 1369–1375 (Jul. 1992).

Derwent Abstract No. 50355C/29 (04.10.78).

Derwent Abstract No. 93–299541/38 (84.08.20).

Derwent Abstract No. 89–250045/35 (30.08.89).

AMINO ACID COMPOSITIONS AND USE THEREOF IN CLINICAL NUTRITION

This application is a continuation of 371 of PCT/EP96/00739, filed Feb. 22, 1996 which is a continuation-in-part of U.S. Ser. No. 08/392,694, filed Feb. 23, 1995, now U.S. Pat. No. 5,656,608.

BACKGROUND OF THE INVENTION

The present invention relates to the use of specific amino acids in the preparation of a medicament or nutritional formulation which may be therapeutically administered to patients suffering from a wide variety of diseases and morbid conditions.

It has now surprisingly been found that, inter alia, glycine is suitable for minimizing and/or preventing the metabolic effects of a wide range of disease states and traumatized or other morbid conditions induced by elevated TNF levels.

In view of the above-mentioned effects, there are provided pharmaceutical compositions, formulations and diets comprising glycine as well as methods of using glycine. For use in the compositions, formulations, diets and methods of the invention, glycine is conveniently employed in free amino acid form, in the form of glycine precursors, in particular alanine or serine, likewise in free amino acid form, in physiologically acceptable salt form of said amino acids, or in form of mixtures of said amino acids and/or physiologically acceptable salts thereof. Glycine is preferably used in free amino acid form, in physiologically acceptable salt form or in the form of a mixture of glycine in free amino acid form with glycine in physiologically acceptable salt form; most preferably glycine is in free amino acid form.

The term "amino acid of the invention" as used hereinafter is meant to refer to glycine, alanine and/or serine, in free amino acid form and/or physiologically acceptable salt form.

SUMMARY OF THE INVENTION

The invention therefore provides the use of at least one amino acid selected from the group consisting of glycine, alanine and serine, or the physiologically acceptable salts thereof, in the preparation of a medicament or nutritional formulation for the diminution of tumor necrosis factor (TNF) levels in patients in whom said levels are elevated beyond those which mediate physiological homeostasis and local inflammation. Such diminuition of TNF levels can i.a. be achieved by inhibition or diminuition of:

(i) Tumour necrosis factor (TNF) production by macrophage-type cells;
(ii) the release of TNF from macrophage-type cells; and/or
(iii) the binding of TNF by TNF receptors.

By "elevated beyond those which mediate physiological homeostasis and local inflammation" is meant an amount of TNF which is more than the minimum required to regulate circadian rhythm of body temperature, sleep and appetite or the minimum required to exert autocrine and paracrine effects in cells neighboring those in which the TNF is produced or secreted, absent systemic inflammatory effects remote from such cells.

The invention still further provides the use of at least one amino acid, selected from the group consisting of glycine, alanine and serine, or the physiologically acceptable salts thereof, in the preparation of a medicament or nutritional formulation to prevent or diminish the macrophage-type cell induced—TNF mediated—production of at least one protein selected from interleukin 1, interleukin 2, interleukin 6, interleukin 8, interleukin 10, endothelial, platelet and leukocyte selectin, leukocyte function associated antigen 1, very late activation antigen 4, intercellular adhesion molecules, platelet factor 4, neutrophil attractant/activation protein, Sialyl-Lewis-X, gamma interferon-induced peptides, macrophage inflammatory proteins alpha and beta, epithelium derived neutrophil attractant, granulocyte chemotactic protein 2, monocyte chemotactic protein 1, vascular cell adhesion molecule 1, and lymphocyte functional antigen 3.

Whilst the use according to the invention relates particularly to those macrophage-type cells located in the blood (monocytes or mono-nuclear phagocytes), liver (Kupffer cells), nervous system (microglial cells), digestive system (mesentery/gut), heart, kidney and bone (bone cell-derived macrophages), all cells which produce, bind or release TNF are targets for the amino acids of the invention. In particular it is envisaged that production by, release from or binding of TNF to lung derived or located macrophages will be affected by administration to the patient of the medicament or formulation according to the invention.

OBJECTS OF THE INVENTION

The invention also provides a method of reducing the risk of death following endotoxic shock and/or hypoxia-reperfusion injury, in particular, in trauma (polytrauma, burn and post-operative patients as well as septic patients) comprising administering effective amounts of an amino acid of the invention. Endotoxic shock and hypoxia-reperfusion injury are both conditions which may result in death of the patient and which involve elevated TNF levels.

The invention furthermore provides the use of at least one amino acid, selected from the group consisting of glycine, alanine and serine, or the physiologically acceptable salts thereof, in the preparation of a medicament or nutritional formulation for preventing or reducing the risk of liver disease due to excessive alcohol consumption and intestinal and pancreatic disorders resulting therefrom in patients in need of such treatment. For this indication the use of glycine and/or serine or physiologically acceptable salts thereof is preferred and the use of glycine or physiologically acceptable salts thereof is particularly preferred.

Still further the invention provides use of at least one amino acid, selected from the group consisting of glycine, alanine and serine, or the physiologically acceptable salts thereof, in the preparation of a medicament or nutritional formulation for preventing or reducing ethanol toxicity in patients in need of such treatment. For this indication the use of glycine and/or serine or physiologically acceptable salts thereof is preferred and the use of glycine or physiologically acceptable salts thereof is particularly preferred.

The invention also provides use of at least one amino acid, selected from the group consisting of glycine, alanine and serine, or the physiologically acceptable salts thereof, in the preparation of a medicament or nutritional formulation for eliminating ethanol from the stomach before entering the systemic blood circulation in patients in need of such treatment.

DETAILED DESCRIPTION OF THE INVENTION

The invention also provides the use of an amino acid of the invention as additive to foods, soft drinks, vitamins or pharmaceutical preparations for treatment of ethanol toxicity and a method of preventing ethanol toxicity employing an effective amount of an amino acid of the invention.

It is preferred that the medicament or formulation is administered to the patient in such an amount that the amino acid of the invention diminishes TNF levels in the circulatory system to below 250pg/ml (±10%), particularly in the case of traumatized patients suffering from severe (second or third degree) burns, in whom there may have been some leakage of bacterial endotoxins into the general circulation absent the overt clinical manifestations of sepsis. It is more preferred that the amino acid of the invention diminishes TNF levels in the circulatory system to below 80 pg/ml (±10%), and still more preferred that the TNF levels are diminished to below 20 pg/ml (±10%). The skilled man is well aware of how such levels may be detected, in particular via known enzyme linked immunosorbant or radioimmuno assays.

The present invention also provides the use of at least one amino acid, selected from the group consisting of glycine, alanine and serine, or the physiologically acceptable salts thereof, in the preparation of a medicament or nutritional formulation for the prevention or diminution of TNF-induced (acturial) allograft rejection. The allograft may be associated with any organ, but the most profound benefits to the patient will be observed in the case of transplantation or injection surgery associated with the lung, heart, liver, gut/mesentery and kidney.

In the case that the medicament or formulation is to be administered to transplant patients, it may advantageously further comprise at least one of the following compounds: neutralizing antibodies raised against TNF, TNF soluble receptors or derivatives or parts thereof, and cyclic polypeptide immuno-suppressants. An example of a well known cyclic polypeptide immuno-suppressant suitable for inclusion in the medicament is cyclosporin, or an effective derivative thereof. A particularly suitable TNF soluble receptor comprises a synthetic dimeric soluble fusion protein construct which combines two p60 TNF receptors with the Fc portion of an IgG molecule. This fusion protein construct possesses a higher affinity and is a superior inhibitor of TNF bioactivity than either native monomeric TNF receptors (p80 or p60) or anti-TNF antibodies.

The nutritional formulation or medicament may be administered either prophylactically, e.g. preoperatively, in the acute phase, e.g. postoperatively, or both.

The nutritional formulation or medicament may be administered to the patient enterally or parenterally. The enteral administration route is preferred, particularly for subsequent or prophylactic treatment; particularly contemplated enteral administration routes are oral administration, nasal administration and/or tube feeding. The medicament or formulation is conveniently administered in the form of an aqueous liquid. The medicament or formulation in a form suitable for enteral application is accordingly preferably aqueous or in powder form, whereby the powder is conveniently added to water prior to use. For use in tube feeding, the amount of water to be added will depend, inter alia, on the patient's fluid requirements and condition. It will be appreciated that, for acute treatment, the parenteral application route is preferred. The parenteral application route is, for example, also indicated where the objective is to control the effects of chronic endotoxemia.

The medicament or formulation may be so formulated as to deliver to the patient from 1 to 80 g of the amino acid of the invention per 24 hours. The amount of medicament or formulation to be administered depends to a large extent on the patients's specific requirements. Such daily amounts of amino acid of the invention are suitable for treatment of the desired effects as well as for prophylactic/pretreatment. In the case that the medicament or formulation comprises a single amino acid of the invention (in the L-configuration), it may be administered to the patient in an amount such that the concentration of that amino acid in the patients's plasma is elevated to between 0.5 and 2.0 mM, preferably from 1.0 to 2.0 mM. Whilst concentrations higher than this are anticipated, it is expected that significant clinical effects will be obtained if the concentration of the acid is increased, as a consequence of administration of the formulation or medicament, so that it lies in the range of from 1.2 to 1.5mM. In traumatic, hypercatabolic patients it may even be beneficial to raise the plasma glycine, serine or alanine levels to about 0.2 to 0.3 mM which corresponds to plasma glycine levels of healthy individuals.

The most preferred amino acid of the invention for incorporation into the medicament or formulation for use according to the invention is glycine or a physiologically acceptable salt thereof.

Generally, it is indicated to use an amino acid of the invention in combination with one or more of the following components:
  (i) omega-3 polyunsaturated fatty acids (PUFAs) where desired in admixture with omega-6 PUFAs;
  (ii) L-arginine or other physiologically acceptable compounds associated with the synthesis of polyamines, or mixtures thereof; and
  (iii) a nucleobase source.

Whereby the use of a medicament or nutritional formulation comprising an amino acid of the invention in combination with arginine or other physiologically acceptable compounds associated with the synthesis of polyamines such as ornithine is preferred. Use of a medicament or nutritional formulation comprising an amino acid of the invention, arginine or ornithine and omega-3 polyunsaturated fatty acids (PUFAs) is also preferred.

Nucleobase sources suitable for use in combination with the amino acids of the invention comprise or consist of natural nucleobases, nucleosides, nucleotides, RNA, DNA, equivalents thereof and/of mixtures comprising one or more of these compounds.

Natural nucleobases include the purines adenine and guanine as well as the pyrimidines cytosine, thymine and uracil. Where the nucleobase source is in the form of free nucleobases, it is preferably uracil.

Natural nucleosides include the ribose nucleosides adenosine, guanosine, uridine and cytidine and the deoxyribose nucleosides deoxyadenosine, deoxyguanosine, deoxythymidine and deoxycytidine.

Natural nucleotides include phosphate esters of natural nucleosides, such as the monophosphates adenylate (AMP), guanylate (GMP), uridylate (UMP), cytidylate (CMP), deoxythymidiylate (dTMP), deoxycytidylate (dCMP), and diphosphates and triphosphates of natural nucleosides such as ADP and ATP.

A purified nucleobase source, such as yeast is preferred. However, other sources such as meat and the like may be used. Preferably the nucleobase source is RNA.

Accordingly, the invention provides medicaments or nutritional formulations comprising effective amounts of:
  (a) an amino acid of the invention (component (a)) in association with one or more components selected from
  (b) omega-3 PUFAs where desired in admixture with omega-6 PUFAs (component (b));

(c) L-arginine or other physiologically acceptable compounds associated with the synthesis of polyamines, or mixtures thereof (component (c)); and (d) a nucleobase source (component (d)).

Said medicaments and nutritional formulations are hereinafter designated "diets of the inventions".

The dosage should be such that the medicaments or nutrional formulations are effective for the diminution of tumour necrosis factor (TNF) levels in patients in whom said levels are elevated beyond those which mediate physiological homeostasis and local inflammation.

One unit dose of such a medicament or nutritional formulation preferably comprises 1.5 to 80 parts by weight of component (a) in association with the following amounts of one or more components selected from (b) to (d): 0.1 to 20 parts by weight of component (b), 3 to 40 parts by weight of component (c) and 0.1 to 4.0 parts by weight of component (d). Particularly preferred one unit dose comprises 1.5 to 80 parts by weight of component (a) in association with the following amounts of one or more components selected from (b) to (d): 2 to 5 parts by weight of component (b), 7.5 to 20 parts by weight of component (c) and 1.7 to 2.0 parts by weight of component (d).

The amount of components (a) to (d) administered daily will conveniently correspond to 1.5 to 80 g for component (a), 0.1 to 20 g, preferably 2 to 5 g, for component (b), 3 to 40 g, preferably 7.5 to 20 g, for component (c) and 0.1 to 4.0 g, preferably 1.7 to 2.0 g, for component (d).

With respect to component (d) the above dosage is indicated for RNA, DNA, nucleosides or nucleotides. For nucleobases one weight unit of nucleobases is regarded to be equivalent to 2.5 to 3.0 weight units of RNA, DNA, nucleosides or nucleotides.

Where medicaments or nutritional formulations comprising an amino acid of the invention in combination with one or more of the above-mentioned components (b), (c) and (d) are used, such medicaments or nutritional formulations will conveniently comprise in one unit dose (a) 1.5 to 80 parts by weight of one or more amino acids selected from the group consisting of glycine, alanine and serine, in free form or physiologically acceptable salt form, or mixtures thereof, in combination with one or more compounds selected from the group consisting of (b) 2 to 5 parts by weight omega-3 polyunsaturated fatty acids;

(c) 7.5 to 20 parts by weight L-arginine or L-ornitine, or mixtures thereof; and (d) 1.7 to 2.0 parts by weight RNA.

Preferred medicaments or nutritional formulations comprise in one unit dose:

(a) from 1.5 to 80 parts by weight of an amino acid selected from the group consisting of glycine, alanine and serine, in free form or physiologically acceptable salt form, or mixtures thereof, in association with (c) 3 to 40 parts by weight, preferably 7.5 to 20 parts by weight, of arginine or an equivalent amount of one or more other physiologically acceptable compounds associated with the synthesis of polyamines, or an equivalent amount of a mixture of arginine with such compounds.

More preferably the medicaments or nutritional formulations of the invention comprise component (a) in combination with component (c) at a weight ratio of 1:2 to 4:1, particularly preferred at a weight ratio of 1:1 to 2:1.

Further preferred medicaments or nutritional formulations comprise in one unit dose:

(a) from 1.5 to 80 parts by weight of an amino acid selected from the group consisting of glycine, alanine and serine, in free form or physiologically acceptable salt form, or mixtures thereof, in association with (b) 0.1 to 20 parts by weight, preferably 2 to 5 parts by weight, of omega-3 PUFAs; and (c) 3 to 40 parts by weight, preferably 7.5 to 20 parts by weight, of arginine or an equivalent amount of one or more other physiologically acceptable compounds associated with the synthesis of polyamines, or an equivalent amount of a mixture of arginine with such compounds.

Omega-3 PUFAs are conveniently protected against peroxidation.

Physiologically acceptable ways of protecting omega-3 PUFAs against peroxidation are known in the art. They include physiologically acceptable micro-encapsulation of omega-3 PUFAs and the use of physiologically acceptable antioxidants.

A typical example suitable for use as physiologically acceptable micro-encapsulation agents is starch. The micro-encapsulation can be effected in a manner known per se. The micro-encapsules may be coated in a manner known per se, by physiologically acceptable coating agents such as Gum Arabic.

Typical examples of antioxidants suitable for use in the method of the invention include antioxidant vitamins such as Vitamin C, Vitamin E or mixtures thereof.

The amount of antioxydant added should be sufficient to prevent peroxidation of the omega-3 PUFAs. Such amounts can be easily calculated. In general, for convenience, any antioxydants employed to prevent peroxidation, will be employed in excess. It will be appreciated that the presence of any other agent administered in association with the omega-3 PUFAs may require adjustment of the amount of antioxidant to be employed.

The omega-3 PUFAs may be employed in a form suitable for the physiological supply of omega-3 PUFAs, e.g. in free acid form, in triglyceride form, or in the form of physiologically acceptable natural sources of omega-3 PUFAs. Such natural sources include linseed oil and fish oils such as menhaden oil, salmon oil, mackerel oil, tuna oil, codliver oil and anchovy oil. Said natural sources, in particular, the fish oils, comprise substantial amounts of omega-3 fatty acids. Where the omega-3 PUFAs are employed in triglyceride form, said triglycerides may comprise esters with other physiologically acceptable fatty acids. Preferred omega-3 PUFAs include eicosapentaenoic acid (EPA) and docosahexaenoic acid (DHA), in free acid form, in triglyceride form or in form of natural sources having a high EPA and/or DHA content.

When the amino acids of the invention are administered in the form of a medicament such a medicament will comprise from 1 to 99 g of the amino acid of the invention per 10 g.

In general, favourable effects are obtained when administering the diets of the invention in the form of a formula diet, which may, depending on the circumstances be a complete formula diet (i.e. a diet supplying essentially all required energy, amino acids, vitamins, minerals and trace elements) or a diet supplement. The diet will conveniently be taken in aqueous liquid form. A formula diet accordingly may comprise a source of carbohydrate lipids fat (fat source) and protein (nitrogen source), and at least one amino acid selected from the group consisting of glycine, L-alanine and L-serine, or physiologically acceptable salts thereof, characterized in that the acid or salt is present in the formula diet in an amount of about 0.5 to 10 g per 100 g. The formula diet will preferably further comprise other nutritionally advantageous components such as vitamins, minerals, trace elements, fibers (preferably soluble fibers).

Examples of suitable nitrogen sources include nutritionally acceptable proteins such as soy bean or whey derived proteins, caseinates, and/or protein hydrolysates. Suitable carbohydrate sources include sugars such as maltodextrins. Examples of suitable fat sources include triglycerides, as well as di- and monoglycerides.

Examples of vitamins suitable for incorporation into the medicament or formulation of the invention include Vitamin E, Vitamin A, Vitamin D, Vitamin K, folic acid, thiamin, riboflavin, Vitamin $B_1$, $B_2$, $B_6$ and $B_{12}$, niacin, biotin and panthotenic acid in nutritionally acceptable form.

Examples of mineral elements and trace elements suitable for incorporation into the medicament or formulation include sodium, potassium, calcium, phosphorous, magnesium, manganese, copper, zinc, iron, selenium, chromium, and molybdenum in nutritionally acceptable form.

In particular, the medicament or formulation will preferably comprise beta-carotene (Vitamin A), Vitamin E, Vitamin C, thiamine, Vitamin $B_{12}$, choline, selenium and zinc in nutritionally acceptable form.

The term "soluble fiber" as used herein refers to fibers which are able to undergo substantial fermentation in the colon ultimately to produce short chain fatty acids. Examples of suitable soluble fibers include pectin, guar gum, locust bean gum, xanthan gum which may optionally be hydrolysed. For adults the total amount of soluble fibre per day will conveniently lie in the range of from 3 to 30 g.

It will be appreciated that omega-3 PUFAs may be administered in higher amounts than those indicated hereinabove, and that such higher amounts will in general not impair the desired effect or provoke undesired side effects.

Compounds particularly suitable for use as component (c) in the formulation of the invention include L-arginine and L-ornithine, most preferably L-arginine. Component (c) may be employed in free form, physiologically acceptable salt form, e.g. in the form of a salt with phosphoric acid, citric acid, tartaric acid, fumaric acid, adipic acid or lactic acid, or in small peptide form. Preferably L-arginine in free form is employed.

The term small peptides as used herein refers to peptides having from 2 to 6, preferably from 2 to 4 amino acids.

As already indicated, omega-3 PUFAs will conveniently be administered in the form of fish oils, protected or not against peroxidation. Such fish oils also comprises omega-6 PUFAs.

Omega-6 PUFAs have also a favourable effect on the immune response and on the resistance to infection upon surgery. Accordingly, diets of the invention will conveniently further comprise omega-6 PUFAs.

For the purpose of the invention the omega-6 PUFAs may be in free acid form or in a form suitable for the physiological supply of omega-6 PUFAs, e.g. in triglyceride form. Examples of omega-6 PUFAs particularly appropriate for use according to the invention, include linoleic acid and arachidonic acid, linoleic acid being most preferred. Examples of suitable omega-6 PUFA sources are known in the art. They include fish oils and vegetable oils. Examples of omega-6 PUFA sources having a high linoleic acid content such as safflower oil, sunflower oil, soya oil, cotton oil and corn oil.

Administration of a daily amount of omega-6 PUFAs in the range of from 1.5 to 5.0 g will in general suffice to attain a favourable effect. One unit dose of the medicaments or nutritional formulation defined above may accordingly further contain 1.5 to 5 parts by weight of omega-6 PUFAs.

In addition to components (b), (c) and (d), and omega-6 PUFAs further components may be added to the diets of the invention and may have a beneficial effect on the activity of the amino acid of the invention. An example of such beneficial components are omega-9 PUFAs. A preferred natural source for such fatty acid mixtures are fish oils. For taste and other reasons, the fish oils will, in oral application forms, preferably be used in encapsulated form.

Where the formula diet of the invention is intended for use as a nutritional supplement (e.g. pre-operative treatment), the amount of energy supplied by it should not be too excessive, in order not to unnecessarily suppress the patients appetite. The supplement should conveniently comprise energy sources in an amount supplying from 600 to 1000 Kcal/day. For use as a complete formula diet (e.g. for post-operative treatment, treatment of trauma), the diets of the invention will conveniently supply from 600 to 1500 Kcal/day. The contribution of the nitrogen source, carbohydrate source and lipid source to the total daily caloric may vary within wide ranges. In preferred formulations of the invention the carbohydrate source provides for 40 to 70% of the total energy supply and, the nitrogen and fatty acid source each for 15 to 30% of the total energy supply of the formulation. For use as complete diet, the diet of the invention will conveniently be administered in aqueous liquid form in volumes in the range of from 500 ml to 3000 ml. For use as a supplement, the administration may be in powder or liquid form.

Conditions or diseases in which patients have elevated TNF levels which can be treated in accordance with the invention include the following: osteoporosis; arthritis; metastasis; lung diseases such as adult respiratory distress syndrome (ARDS); inflammatory bowel diseases such as ulcerative colitis and Crohn's disease; coronary artery disease; liver cirrhosis—whether alcohol or viral induced; sepsis, including endotoxic shock; hypoxia reperfusion injury; the wasting syndrome observed in AIDS and cancer patients; hepatitis; nephritis; pathological angiogenesis; treatments such as radiation and chemotherapy which—for example—prejudice bone marrow; organ rejection; trauma; post-ischemic heart injury; ulcers; degenerative conditions such as motor neurone disease and multiple sclerosis which are associated with the nervous system; brain injury and inflammation; pancreatitis; renal failure; diabetes; stroke; asthma and infection. Especially good results are achieveable in the treatment of sepsis, endotoxic shock, infection and hypoxia reperfusion injury, particularly of endotoxic shock and sepsis. Also particularly good results are achievable in the treatment of inflammatory bowel diseases, sepsis, chronic liver diseases, pathological angiogenesis, arteriosclerosis and trauma. Infections may be wound infections, empyemas, bacteremias, abscesses, septicemias and the like. They may be caused by a variety of infectious agents, including bacteria, viruses, parasites, fungi and endotoxins.

Generally speaking, the treatment with the amino acid of the invention is indicated for patients in whom TNF levels could be/are at least transiently elevated above those levels which mediate physiological homeostasis and local inflammation. Such patients include e.g. trauma patients (polytrauma, burns, major surgery); patients with systemic inflammatory response syndrome (SIRS); septic patients; adult respiratory distress syndrome (ARDS) patients; patients with acute liver failure in whom no pretreatment is possible but an acute effect is desired; patients at infection risk such as patients having a lowered resistance due to immunosuppression, patients subject to radio- and/or chemotherapy, patients suffering from diabetes mellitus, from protein-malnourishment, gastrointestinal cancer surgery patients, cardiac surgery patients, patients subject to transplantations, patients having an increased risk of liver disease due to excessive alcohol consumption and patients suffering from human immunodeficiency virus-related infection; and patients before and following major operative procedures, i.e. any operative procedure requiring general anesthesia such as cardiac bypass surgery and major upper gastrointestinal surgery.

Administration of a medicament or nutritional formulation containing an amino acid of the invention in combination with component (c) is particularly indicated for the treatment of osteoporosis.

The surprising pharmacological activity of glycine, or the amino acid of the invention respectively, of diminishing TNF levels in patients in whom said levels are elevated beyond those which mediate physiological homeostasis and local inflammation is useful, in that it allows i.a. to minimize the effects of endotoxemia, hypoxia-reperfusion injury and infection and to reduce the risks of endotoxic shock and sepsis, and thus reduce or prevent the risk of mortality.

The amino acids of the invention and especially the diets of the invention are as already set out above particularly suitable for treatment of patients due for surgery. Such pretreatment will be most effective when administering the diet of the invention in the form of a supplement. The supplement will advantageously be administered over a period of 3 days or longer. In general, a pretreatment starting 3 to 6 days before surgery, and during said 3–6 day period will be sufficient to attain the desired effect. For pretreatment or prophylactic purposes administration of a supplement containing from 1.5 g to 80 g amino acid of the invention in association with from 2 to 5 g Component (b) (omega-3-PUFAs) and/or with Component (c) supplying from 7.5 to 20 g L-arginine or L-omithine per day, will in general give the desired effect.

Such a supplement may and preferably will also contain an effective amount of component (d), omega-6 PUFAs or further components as set out above.

The supplement will conveniently be administered in the form of unit doses suitable for administration of the supplement 3 to 4 times per day. Where the diets of the invention comprise energy sources, it is appropriate not to supply more than 1500 Kcal/day. Apart from this limitation with respect to the energy supply, diet supplements of the invention for diminuition of TNF levels can and will conveniently be supplied in the form of complete formula diets as described above.

Where acute treatment of patients following excessive ethanol exposure is necessary, the amino acid of the invention will conveniently be administered parenterally. Typical administration forms suitable for such acute treatment are e.g. the aqueous solutions disclosed hereinbelow.

Where it is desired to minimize alcohol uptake into the blood by glycine induced alcohol elimination in the stomach, the amino acid of the invention will conveniently be provided in a conventional oral administration form, such as granules, tablets, capsules, liquids (including soups and drinks such as soft drinks, thirst quenchers), powders, formula diets etc. When formulated in a physiologically acceptable formulation form such as a capsule or tablet form, such formulations will conveniently contain 0.2 to 90% by weight, preferably from 30 to 50% by weight of an amino acid of the invention. In general, satisfactory alcohol (ethanol) elimination from the stomach is obtained when administering a total amount within the range of from 0.01 to 5.0 g of one or more of the amino acids selected from the group consisting of glycine, alanine and serine, in free form and/or physiologically acceptable salt form per kg body weight. The administration is conveniently orally, and prior to alcohol intake.

Typical pharmacologically acceptable formulation forms for oral administration will further comprise pharmacologically acceptable diluents, carriers, vitamins, spices, pigments and/or other adjuvants well known to the skilled person to be suitable for incorporation into such formulation.

The diets and formulations of the invention may be obtained in a manner known per se, e.g. by admixing the ingredients.

Typical formulations suitable for use according to the invention and in particular for treatment of patients having increased risk of liver diseases due to excessive alcohol consumption include aqueous solutions consisting essentially of 0.1% to 90% by weight of at least one amino acid selected from the group consisting of glycine, alanine and serine, and pharmaceutically acceptable salts thereof, the balance being distilled water. The amino acid of the invention may be present in a concentrated form of the solution in an amount of from 15 to 90% (by weight of the solution). Concentrated solutions are suitable for dilution to application forms or for use in acute treatment. Application forms having a lower content (e.g. 0.1 to 5%) of the amino acid of the invention will in general be indicated for prophylactic purposes; concentrated forms of the solution having a higher content (e.g. 5% to 40% by weight) of amino acid of the invention will in general be more suitable for acute treatment.

Other formulations suitable for inclusion in the medicament or formulation of the invention, in particular for parenteral application, include infusion solutions such as Ringer's injection solution, lactated Ringer's injection solution, crystalloids, colloids or other plasma substitutes, in association or enriched with about 0.1 to 5.0 g per liter infusion solution of glycine, serine and/or alanine. Ringer's injection solution is a sterile solution, containing from 3.23 to 3.54 g of sodium (equivalent to from 8.2 to 9.0 g of sodium chloride), from 0.149 to 0.165 of potassium (equivalent to from 0.285 to 0.315 g of potassium chloride), from 0.082 to 0.098 g of calcium (equivalent to from 0.3 to 0.36 g of calcium chloride, in the form of $CaCl_2.2H_2O$), from 5.23 to 5.80 g of chloride (as NaCl, KCl and $CaCl_2.2H_2O$) and water in sufficient quantity to give 1000 ml solution. Lactated Ringer's Injection solution is a sterile solution containing from 2.85 g to 3.15 g sodium, as chloride and lactate), from 0.141 to 0.173 g of potassium (equivalent to from 0.27 g to 0.33 g of potassium chloride), from 0.049 to 0.060 g calcium (equivalent to from 0.18 g to 0.22 g of $CaCl_2.2H_2O$), from 2.31 g to 2.61 g of lactate, from 3.68 to 4.08 g of chloride (as NaCl, KCl and $CaCl_2.2H_2O$) and water in sufficient quantity to give 1000 ml solution.

The terms crystalloids and colloids in connection with fluid therapy are known in the art. They include plasma substitutes such as Haemaccel (polygeline based) and Gelofusine (gelatin based).

The invention will be further understood by reference to the following specific description.

EXAMPLE 1

Effects of Dietary Glycine on Survival and Liver Injury in the Rat

Male Sprague-Dawley rats (200–250 g) are fed, ad libitum, by powder diet containing 20% by weight of casein (control diet) or 5% by weight of glycine and 15% by weight of casein (glycine diet) for 3 days prior to injection with LPS. The rats are then injected with lipopolysaccharide (LPS; 10, 20 and 30 mg/kg resp.) via the tail vein and mortality is assessed 24 hours after the injection. If the rats survive 24 hours, they are considered safe as no late mortality is observed.

Results a) The 5% glycine diet offers a 100% protection against an LPS dose of 10 mg/kg compared to 50% mortality in the control group significant at the p<0.05 level. At an LPS dose of 20 mg/kg a 30% mortality is observed with 5% glycine diet and a 70% mortality with the control diet. At 30 mg/kg LPS mortality increased to 90% in the glycine treated animals and to 100% in the controls.

b) From the survivors, the liver enzyme AST (Aspartate Aminotransferase; a transaminase) is measured as an indication of liver damage. The AST level is markedly and significantly reduced in the glycine fed rats (from 2000IU/L in untreated fed rats treated with an LPS dose of 10 mg/kg).

c) In a parallel experimental series, the effect of glycine diet on tumor necrosis factor (TNF) is assessed. Serum TNF was measured by ELISA. After injection of 10 mg/kg LPS, serum TNF increased rapidly in rats fed with the control diet to values over 6000 pg/ml, 60 min after injection, before declining to control values. This increase is significantly suppressed (by at least 50%; p<0.05) in rats fed with the 5% glycine diet, whereby the peak is attained 150 min after injection.

d) Liver and lung specimens for histology are taken 24 hr after injection of LPS (10 mg/kg) and hematoxylin-eosin stained. Rats fed with the control diet show many necrotic areas and neutrophil infiltration in the liver and marked interstitial edema with neutrophil infiltration in the lung. Rats fed with glycine diet show less necrosis in the liver and less pulmonary edema than rats fed with the control diet.

e) Serum glycine concentration is determined by HPLC from 2 groups of rats fed with control diet and glycine diet resp., and of which each group had been given a LPS injection (10 mg/kg i.v. in the tail vein). A rat fed with glycine diet without LPS treatment shows a remarkably higher glycine concentration (1892 $\mu$M) than rats fed with control diet (150 $\mu$M) and without LPS injection. The rats fed with glycine diet maintain the high concentration of glycine (1727±515 $\mu$M) 6 hr after LPS injection; the rats fed with control diet have 6 hr after the LPS injection a serum glycine concentration of 278 $\mu$M.

EXAMPLE 2

Effects of Glycine on Reperfusion Injury in a Low Flow-reflow Liver Perfusion Model Methods Animals used. Male Sprague-Dawley rats weighing between 180–210 g and fed a Purina diet. Rats are fasted for 24 h prior to surgery.

Liver Perfusion. Rats are anesthetized with pentobarbital sodium (50 mg) before surgery and livers are removed surgically and perfused via a cannula inserted into the portal vein with Krebs-Henseleit bicarbonate buffer (pH 7.4, 37° C.) saturated with an oxygen-carbon dioxide (95:5) mixture in a non-recirculating system (Krebs-Henseleit, 1932). After surgery, livers are perfused at flow rates around 1 ml/g/min for 75 minutes (low-flow). Subsequently, livers are perfused at normal flow rates (4 ml/g/min) for 40 minutes (reflow). Glycine is dissolved in Krebs-Henseleit bicarbon buffer (pH 7.4, 37° C.) and infused into the liver continuously beginning 10 minutes before reflow at rates resulting in final concentrations ranging from 0.06–2 mM.

Lactate dehydrogenase (LDH). LDH activity in the perfusate is determined using standard enzymic techniques (Bergmeyer, 1988). Three ml of perfusate are mixed thoroughly with a reagent containing 15% trichloroacetic acid, 0.375% thiobarbituric acid and 0.25N hydrochloric acid and heated for 15 minutes in a boiling water bath. After cooling, samples were centrifuged at 1000 g for 10 minutes and the absorbance of the supernatant is determined at 535 nm. Rates of release of LDH are expressed per gram wet weight of liver per hour.

Trypan Blue Distribution Time and Histological Procedures. To assess microcirculation and cell death in the liver, trypan blue is infused into the liver at the end of all experiments at final concentrations of 0.2 mM (Belinsky et al., 1984). The time for the liver surface to turn evenly dark blue is recorded. Excess dye is removed by perfusion with Krebs-Henseleit buffer for an additional 10 minutes. Subsequently, livers are perfused with 1% paraformaldehyde for 10 minutes and fixed tissue is embedded in paraffin and processed for light microscopy. Sections are stained only with eosin, a cytoplasmic stain, so that trypan blue can be identified readily in the nuclei of damaged cells.

All nuclei of parenchymal cells in a zone radiating five cells from either periportal or pericentral regions are identified as trypan blue positive or negative. The percentage of staining is calculated from the number of stained nuclei divided by the total number of cells in any given region.

Statistical Analysis. Student's-t-test or ANOVA was used where appropriate. Differences are considered significant when the p-value is less than 0.05.

Results

Effects of Glycine on Hepatocellular Damage in a Low-flow, Re-flow Perfusion Model. During the low-flow period, LDH release is minimal (around 1 IU/g/h at 75 minutes). When the flow rate is increased to 4 ml/g/min, however, LDH release increases gradually, reaching a new steady-state value in about 30 minutes. Maximal LDH release during the reperfusion period is around 35 IU/g/h controls, but is reduced significantly by glycine treatment in a dose-dependent manner. When the concentration of glycine is increased to 2 mM, LDH release is reduced to around 5 IU/g/h; half-maximal decreases occur with 180 $\mu$M glycine.

Trypan blue uptake indicates irreversible loss of cell viability in the liver lobule. Reflow for 40 minutes following 75 minutes of low-flow hypoxia causes death in about 30% of parenchymal cells in pericentral regions, but only affected about 2% of cells in previously normoxic periportal regions. Infusion of glycine (2 mM) decreases cell death in pericentral areas to 9%. Taken together, reperfusion injury, which occurs when oxygen is re-introduced into previously anoxic pericentral regions of the liver lobules, is clearly reduced by acute glycine infusion in a dose-dependent manner.

Effects of Glycine on Trypan Blue Distribution. Trypan blue distribution time, an indicator of the hepatic microcirculation, is slightly but significantly lower in glycine-infused livers than in controls (about 190 seconds in glycine-treated liver and 225 seconds in controls, respectively, p<0.05, n=5) when trypan blue is infused into the liver 5 minutes after reperfusion. However, values are reduced dramatically by glycine in a dose-dependent manner when trypan blue is infused at the end of 40 minutes of reperfusion. It took about 460 seconds for trypan blue to distribute evenly in controls, whereas values are reduced to about 250 seconds when 2 mM glycine is infused. The concentration which caused half-maximal decrease in trypan blue distribution time is also around 180 $\mu$M.

Glycine minimizes LDH release and cell death almost completely during reperfusion in a dose-dependent manner.

Glycine has accordingly potent cytoprotective effects against reperfusion injury in a low-flow, reflow liver perfusion model in the rat.

Trypan blue distribution time is reduced by glycine in a dose-dependent manner, with the half-maximal effect similar to the cytoprotective effect of glycine (180 μM). Since trypan blue distribution time can be influenced not only by disturbances of the hepatic microcirculation but also by hepatic cell injury, trypan blue distribution time is measured after only 5 minutes of reflow, when reperfusion injury is minimal. This value is also reduced significantly by glycine but to a smaller extent, indicative of improved hepatic microcirculation.

Other possible mechanisms related to anoxia and reperfusion injury such as ATP depletion and alteration of mitochondrial function are also investigated. Bile production, a highly energy-dependent process, is not affected by glycine, indicating that glycine does not minimize ATP depletion, and oxygen uptake, an indicator of mitochondrial function, is not altered by glycine either. In conclusion, glycine improves hepatic microcirculation and protects against oxygen-dependent reperfusion injury.

EXAMPLE 3

Effect of Pre-treatment with Glycine on the Mortality after Partial Hepatic Ischemia/Reperfusion and LPS Injection After 3 days feeding with control diet and glycine diet resp., rats are given partial hepatic ischemia for 90 min. under methoxyflurane anesthesia. A sublethal dose of LPS (5 mg/kg) is injected via the tail vein 6 hr after reperfusion.

Results

All of the control rats without LPS injection survived for 24 hours after 90 min. partial hepatic ischemia/reperfusion (n=4). All rats fed with control diet and with 90 min. partial hepatic ischemia/reperfusion die within 24hr after the (sublethal) LPS injection (n=4).

Pretreatment of rats with glycine diet markedly improved the survival (5 rats out of 6 survived) under the same conditions (90 min. partial hepatic ischemia/reperfusion and given the LPS injection) during the observation period (24 hours from the injection time); $p<0.05$ with Fisher's test).

EXAMPLE 4

Effects of Dietary Glycine on Alcohol-induced Liver Injury 4.1 Materials and Methods a. Animals In Male Wistar rats, weighing 300 to 320 mg each, intragastric cannulas were inserted as described by Tsukamoto and French. Cannulas were tunnelled subcutaneously to the dorsal aspect of the neck and attached to infusion pumps by means of a spring-tether device and swivel allowing complete mobility of rats in metabolic cages. Animals were infused continuously with a high-fat liquid diet containing ethanol for up to 4 weeks. All animals received humane care in compliance with institutional guidelines.

b. Diet

A liquid diet described by Thompson and Reitz was used. It contained corn oil as fat (37% of total calories), protein (23%), carbohydrate (5%), minerals and vitamins, plus ethanol or isocaloric maltose-dextrin (35%), hereinafter designated liquid control diet. Glycine (2 or 5% by weight) was added to the liquid control diet; such diets are hereinafter referred to as liquid 2% glycine diet and liquid 5% glycine diet resp.

c. Urine Collection and Assay of Ethanol

Concentration of ethanol in urine, which are representative of blood alcohol levels were measured daily. Rats were housed in metabolic cages that separated urine from feces, and urine was collected over 24 hours in bottles containing mineral oil to prevent evaporation. Each day at 0900 h, urine collection bottles were changed and an 1-ml sample was stored at −20° C. in a microtube for later ethanol analysis. Ethanol concentration was determined by measuring absorbance at 360 nm resulting from the reduction of $NAD^+$ to NADH by alcohol dehydrogenase.

d. Blood Collection and Asparate Aminotransferase (AST)

Blood was collected via the tail vein once a week and centrifuged. Serum was stored at −20° C. in a microtube until assayed for AST by standard enzymatic procedures. Whole blood (100 μl) was also assayed for ethanol as described below, and hepatic portal blood was also collected when the liver biopsy were performed at the 2nd and 4th week of treatment with ethanol.

e. Ethanol Assay in Breath, Peripheral and Portal Blood, Feces and Stomach Contents To determine concentrations of ethanol in breath, rats were forced to breathe into a closed heated chamber (37° C.) for 20 sec. and 1 ml of breath was collected with a gas-tight syringe. Ethanol concentrations were analysed by gas chromatography (GC). Ethanol in peripheral and portal blood was also assayed by GC. Blood (100 μl) was mixed with 900 μl of distilled water in a closed flask incubated for 30 min. at 37° C., and 1 ml of the gas phase was collected and assayed by GC. Rat feces were collected directly from the anus, homogenized in distilled water and incubated and analysed as described above for blood. Stomach contents were also collected when rats were sacrificed at the 4th week of ethanol treatment, and analysed as described for blood.

f. Measurement of Glycine Concentration in Blood

After 4 weeks of ethanol treatment, 500 μl of plasma was collected and stored at −80° C. for determination of glycine concentration in blood by HPLC. Quantitative analysis of glycine in heparinized plasma was carried out using the PICP-TAG (Waters, Milford, Mass.) method. Plasma samples were first hydrolysed with HCl, and then derivatized with phenylisothiocyanate (PITC) to produce phenylthiocarbamyl (PTC) amino acids. Amino acids including glycine were determined by automated gradient reserve phase high-pressure liquid chromatography (HPLC).

g. Pathological Evaluation

Rats underwent liver biopsy and autopsy after 2 and 4 weeks of treatment with ethanol. Livers were formalin-fixed, embedded in paraffin and stained with hematoxylin and eosin to assess steatosis, inflammation and necrosis. Liver pathology was scored as described by Nanji et al. as follows: steatosis (the percent liver cells containing fat): <25%=1+; <50%=2+; <75%=3+, >75%=4+; inflammation and necrosis: 1 focus per low-power field=1+; 2 more=2+.

h. Statistics

ANOVA or Student's t-test was used for determination of statistical significance as appropriate. For comparison of pathological scores, the Kruskal-Wallis ANOVA for ranks was used. A p value less than 0.05 was selected before the study as the level of significance.

4.2 Results

Body weights of rats fed with the liquid control diet, the liquid/glycine diet and the liquid 5% glycine diet, during the course of this study had a tendency to decline during the first week was observed. The body weights then stabilized and were constant during the following 3 weeks of treatment with ethanol. There were no significant differences in body weight among the groups studied.

Ethanol intake was gradually increased to 9 to 10 gm/kg/day during the first week after surgery. Intake was between 10 and 13 gm/kg/day during weeks 2–4, and there were no significant differences between the groups. Glycine concentration in plasma after 4 weeks of treatment was 779±66 $\mu$mol/L in rats receiving the liquid 5% glycine-containing diet, and was 198±16 $\mu$mol/L in ethanol fed rats.

Representative plots of daily urine alcohol concentrations in rats fed with the liquid control diet and the liquid glycine diets were determined. Alcohol levels fluctuate in a cyclic pattern from near zero to greater than 300 mg/dl in rats fed with the liquid control diet, even though ethanol was infused continuously. In rats fed with one of the liquid glycine diets, alcohol concentrations were very low but were still cyclic. Mean urine alcohol concentrations were reduced significantly in a dose-dependent manner; a 50% reduction of the mean urine alcohol concentration was obtained by feeding with the liquid 2% glycine diet, a 70% reduction with the liquid 5% glycine diet.

Serum AST in rats fed with the liquid control diet increased gradually with time of exposure and reached a level of 183 IU/L after 4 weeks (control value 70 IU/L). This increase was attenuated significantly by both glycine treatments at every point during the study. After 4 weeks of treatment, serum AST level was 66 IU/L in 2% glycine-treated rats fed with the In rats fed with the liquid control diet, slight steatosis was observed after only 2 weeks of treatment. After 4 weeks of treatment with said liquid control diet, obvious fatty changes were not apparent in control rats, not treated with ethanol. In rats fed with liquid 2% glycine and liquid 5% glycine diet, fatty changes were attenuated and necrosis and inflammation were almost totally absent. The reductions of steatosis and necrosis were statistically significantly after feeding with the liquid glycine diets; only a tendency for reduction of inflammation was observed after feeding with the liquid glycine diets because of variability.

Eventually, alcohol in stomach contents in glycine-treated rats was also reduced dramatically. Therefore, it is clear that glycine reduces the ethanol concentration in the stomach, possibly by effects on ethanol metabolism.

EXAMPLE 5

Enteral Compositions

In the following compositions MM stands for "mineral mixture", SM for "trace element mixture" and VM for "vitamin mixture". The composition of these three mixtures is as follows:

| Ingredients | g/100 g |
|---|---|
| MM | |
| Maltodextrins | 34.40 |
| Potassium citrate/phosphate | 34.60 |
| Magnesium dicitrate | 8.20 |
| Calcium chloride | 8.00 |
| Sodium citrate/chloride | 9.00 |
| Citric acid | 3.50 |
| Choline tartrate | 2.30 |
| VM | |
| Maltodextrins | 43.44 |
| Sodium ascorbate | 35.00 |
| Vitamin E-Ac. 50% | 16.00 |
| Niacinamide | 1.55 |
| Vitamin A-Acetate | 1.20 |
| Ca-D-Panthothenat | 0.98 |
| Vitamin $K_1$ 1% | 0.71 |
| Vitamin $B_{12}$ 0.1% | 0.30 |
| Vitamin $D_3$ | 0.28 |
| Vitamin $B_6$ | 0.20 |
| Vitamin $B_1$ | 0.17 |
| Vitamin $B_2$ | 0.15 |
| Folic acid | 0.02 |
| Biotin | 0.01 |
| SM | |
| Maltodextrins | 47.79 |
| Molybdenum-yeast | 18.00 |
| Chromium-yeast | 9.20 |
| Zinc sulfate | 7.00 |
| Selenium-yeast | 7.00 |
| Ferrum (II) sulfate | 6.92 |
| Copper (II) gluconate | 2.24 |
| Manganese (II) sulfate | 1.12 |
| Sodium fluoride | 0.70 |
| Potassium iodide | 0.03 |
| Composition Comprising Glycine | |
| Water | 77.40 |
| Maltodextrins | 10.10 |
| Na/Ca caseinates | 4.60 |
| Glycine | 3.00 |
| MM | 2.00 |
| SM | 0.05 |
| VM | 0.10 |
| β-Carotine | 0.03 |

TABLE 1

Effect of Glycine on ethanol concentrations in rats on the Tsukamoto-French Model

| Treatment | Breath | Feces | Urine A.M. | Urine 24 hr | Blood Tail | Stomach Portal Vein | |
|---|---|---|---|---|---|---|---|
| Ethanol | 108 ± 12 | 82 ± 21 | 184 ± 12 | 211 ± 16 | 199 ± 45 | 357 ± 65 | 761 ± 625 |
| Ethanol + 5% Glycine | 5 ± 4*** | 15 ± 11* | 26 ± 25** | 24 ± 8*** | 21 ± 13** | 10 ± 7*** | 26 ± 41* |

Breath, feces, blood and stomach contents were collected from rats and analysed by headspace gas chromatography. Urine samples were analysed enzymatically. Samples are taken from a total of 6 rats. Results are expressed as Mean ± S.E.M.
*$p < 0.05$; $p < 0.01$; *$p < 0.001$ for comparisons of ethanol vs. ethanol + glycine-fed rats values by Student's t-test.

| Ingredients | g/100 g |
|---|---|
| Lipids: | |
| Palm oil | 2.33 |
| Sunflower oil | 0.26 |
| Emulsifier Nathin E | 0.13 |
| | 100.00 |
| Composition Comprising Glycine and Arginine | |
| Water | 77.40 |
| Maltodextrins | 8.93 |
| Na/Ca caseinates | 4.60 |
| Glycine | 3.00 |
| Arginine | 1.17 |
| MM | 2.00 |
| SM | 0.05 |
| VM | 0.10 |
| β-Carotine | 0.03 |
| Lipids: | |
| Palm oil | 2.36 |
| Sunflower oil | 0.23 |
| Emulsifier Nathin E | 0.13 |
| | 100.00 |
| Composition Comprising Glycine and Fish Oil (ω-3 fatty acids) | |
| Water | 77.40 |
| Maltodextrins | 10.10 |
| Na/Ca caseinates | 4.60 |
| Glycine | 3.00 |
| MM | 2.00 |
| SM | 0.05 |
| VM | 0.10 |
| β-Carotine | 0.03 |
| Lipids: | |
| Palm oil | 1.32 |
| Sunflower oil | 0.23 |
| Emulsifier Nathin E | 0.13 |
| Fish Oil EPAX 3000 TG | 1.04 |
| | 100.00 |
| Composition Comprising Glycine and RNA | |
| Water | 77.40 |
| Maltodextrins | 9.96 |
| Na/Ca caseinates | 4.60 |
| Glycine | 3.00 |
| Yeast extract RNA | 0.14 |
| MM | 2.00 |
| SM | 0.05 |
| VM | 0.10 |
| β-Carotine | 0.03 |
| Palm oil | 2.33 |
| Sunflower oil | 0.26 |
| Emulsifier Nathin E | 0.13 |
| | 100.00 |
| Composition Comprising Glycine, Arginine and Fish Oil (ω-3 fatty acids) | |
| Water | 77.40 |
| Maltodextrins | 8.93 |
| Na/Ca caseinates | 4.60 |
| Glycine | 3.00 |
| Arginine | 1.17 |
| MM | 2.00 |
| SM | 0.05 |
| VM | 0.10 |
| β-Carotine | 0.03 |
| Lipids: | |
| Palm oil | 1.32 |
| Sunflower oil | 0.23 |
| Emulsifier Nathin E | 0.13 |
| Fish Oil EPAX 3000 TG | 1.04 |
| | 100.00 |
| Composition Comprising Glycine, Arginine and RNA | |
| Water | 77.40 |
| Maltodextrins | 8.79 |
| Na/Ca caseinates | 4.60 |
| Glycine | 3.00 |
| Arginine | 1.17 |
| Yeast extract RNA | 0.14 |
| MM | 2.00 |
| SM | 0.05 |
| VM | 0.10 |
| β-Carotine | 0.03 |
| Lipids: | |
| Palm oil | 2.33 |
| Sunflower oil | 0.26 |
| Emulsifier Nathin E | 0.13 |
| | 100.00 |
| Composition Comprising Glycine, RNA and Fish Oil (ω-3 fatty acids) | |
| Water | 77.40 |
| Maltodextrins | 9.96 |
| Na/Ca caseinates | 4.60 |
| Glycine | 3.00 |
| Yeast extract RNA | 0.14 |
| MM | 2.00 |
| SM | 0.05 |
| VM | 0.10 |
| β-Carotine | 0.03 |
| Lipids: | |
| Palm oil | 1.32 |
| Sunflower oil | 0.23 |
| Emulsifier Nathin E | 0.13 |
| Fish Oil EPAX 3000 TG | 1.04 |
| | 100.00 |
| Composition Comprising Glycine, Arginine, RNA and Fish Oil (ω-3 fatty acids) | |
| Water | 77.40 |
| Maltodextrins | 8.79 |
| Na/Ca caseinates | 4.60 |
| Glycine | 3.00 |
| Arginine | 1.17 |
| Yeast extract RNA | 0.14 |
| MM | 2.00 |
| SM | 0.05 |
| VM | 0.10 |
| β-Carotine | 0.03 |
| Lipids: | |
| Palm oil | 1.32 |
| Sunflower oil | 0.23 |
| Emulsifier Nathin E | 0.13 |
| Fish Oil EPAX 3000 TG | 1.04 |
| | 100.00 |

As already set out above fish oil is a natural source for omega-3 PUFAs whereas sunflower oil is a natural source for omega-6 PUFAs.

Whilst the invention has been exemplified with reference to the capacity of glycine to suppress an increase in TNF and thereby minimize the effects of endotoxic shock and ischemic reperfusion injury in rats, the skilled man having had the benefit of the present disclosure will appreciate that the invention includes further aspects in addition to those specifically disclosed. For example, the invention further provides the use of at least one amino acid—or precursor thereof, selected from the group consisting of glycine, alanine and serine, or the physiologically acceptable salts thereof, to potentiate synergistically the immunosuppressive effects of cyclic polypeptide immuno-suppressants, neutralizing antibodies which have been raised against TNF or soluble TNF receptors. Such use may also provide a safening effect in respect of the immuno-suppressant, which may be cyclosporin or FK-506, for example. Moreover, patients suffering from a wide variety of diseases and/or conditions may benefit from administration to them of the medicament or formulation of the invention. Such diseases and conditions include: osteoporosis; arthritis; metastasis; ARDS/lung disease; inflammatory bowel diseases such as ulcerative colitis and Crohn's disease; coronary artery disease; liver cirrhosis—whether alcohol or viral induced; sepsis, including endotoxic shock; the wasting syndrome observed in AIDS and cancer patients; hepatitis; nephritis; pathological angiogenesis; treatments such as radiation and chemotherapy which—for example—prejudice bone marrow; organ rejection; trauma; post-ischemic heart injury; ulcers; degenerative conditions such as motor neurone disease and multiple sclerosis which are associated with the nervous system; brain injury and inflammation; pancreatitis; renal failure; diabetes; stroke and asthma.

We claim:

1. A method for treating a human having elevated tumor necrosis factor levels comprising administering to the human a composition comprising an amount of at least one amino acid selected from the group consisting of glycine, alanine and serine, or the physiologically acceptable salts thereof, effective for the diminution of tumor necrosis factor tumor necrosis factor levels in the human.

2. The method according to claim 1 wherein such diminution of tumor necrosis factor levels is achieved by inhibition or diminution of:
   (i) Tumor necrosis factor production by macrophage-type cells;
   (ii) the release of tumor necrosis factor from macrophage-type cells; and/or
   (iii) the binding of tumor necrosis factor by tumor necrosis factor receptors; the macrophage-type cells being selected from the group consisting of monocytes or mono-nuclear phagocytes, Kupffer cells, microglial cells, mesentery/gut, and bone cell-derived macrophages.

3. A method for the diminution of tumor necrosis factor (TNF) levels in patients in whom said levels are elevated beyond those which mediate physiological homeostasis and local inflammation comprising the administration to patient of a medicament or nutritional formulation comprising at least one amino acid selected from the group consisting of glycine, alanine and serine, or the physiologically acceptable salts thereof in an amount which is effective for diminishing said TNF levels.

4. The method according to claim 3 wherein such diminution of TNF levels is achieved by inhibition or diminution of:
   (i) Tumor necrosis factor (TNF) production by macrophage-type cells;
   (ii) the release of TNF from macrophage-type cells; and/or
   (iii) the binding of TNF by TNF receptors; the macrophage-type cells being selected from the group consisting of monocytes or mono-nuclear phagocytes, Kupffer cells, microglial cells, mesentery/gut, and bone cell-derived macrophages.

5. The method according to claim 4 for preventing or reducing the risk of liver disease due to excessive alcohol consumption and intestinal and pancreatic disorders resulting therefrom.

6. The method according to claim 4 for preventing or reducing ethanol toxicity.

7. The method according to claim 4 for eliminating ethanol from the stomach before entering the systemic blood circulation.

8. The method according to claim 4 for the prevention or diminuition of TNF-induced allograft rejection.

9. The method according to claim 4 for the treatment of chronic liver diseases.

10. The method according to claim 4 for the treatment of liver cirrhosis, whether alcohol or viral induced and/or hepatitis.

11. A method for potentiating synergistically the immunosuppressive effects of cyclic polypeptide immunosuppressants comprising the administration to a patient of a medicament or nutritional formulation comprising at least one amino acid selected from the group consisting of glycine, alanine and serine, or the physiologically acceptable salts thereof in an amount which is effective for potentiating the immunosuppressive effects of cyclic polypeptide immuno-suppressants.

12. The method according to claim 11, wherein the amino acid provides a safening effect in respect of the immuno-suppressant.

13. The method according to claim 11 wherein the immuno-suppressant is a cyclosporin or FK-506.

14. A kit of parts comprising one or more of the amino acids selected from the group consisting of glycine, alanine and serine, in free form or physiologically acceptable salt form, or mixtures thereof and a cyclic polypeptide immuno-suppressant as a combined preparation for the simultaneous, separate or subsequent use in the treatment of transplant patients.

15. A kit of parts according to claim 9 for use in the prevention or diminuition of TNF-induced allograft rejection.

16. A kit of parts comprising one or more of the amino acids selected from the group consisting of glycine, alanine and serine, in free form or physiologically acceptable salt form, or mixtures thereof and a cyclic polypeptide immuno-suppressant as a combined preparation for the simultaneous, separate or subsequent use to potentiate synergistically the immunosuppressive effects of the cyclic polypeptide immuno-suppressants.

17. The method according to claim 3 for the treatment of a disease or condition associated with elevated tumor necrosis factor (TNF) levels, in which the disease or condition is selected from the group consisting of: osteoporosis; arthritis; metastasis; lung diseases including adult respiratory distress syndrome (ARDS); inflammatory bowel diseases including ulcerative colitis and Crohn's disease; coronary artery disease; alcohol- or viral-induced liver cirrhosis; sepsis, including endotoxic shock; hypoxia reperfusion injury; the wasting syndrome observed in AIDS and cancer patients; hepatitis; nephritis; pathological angiogenesis; post treatment syndromes following radiation or chemotherapy treatments, including prejudiced bone marrow; organ rejection; trauma; post-ischemic heart injury; ulcers; degenerative conditions such as motor neurone disease and multiple sclerosis which are associated with the nervous system; brain injury and inflammation; pancreatitis; renal failure; diabetes; stroke; asthma and infection.

18. The method according to claim 17 for minimizing the effects of endotoxemia, hypoxia-reperfusion injury and infection.

19. The method according to claim 17 for reducing or preventing the risk of mortality by reducing the risks of endotoxic shock and sepsis.

* * * * *

UNITED STATES PATENT AND TRADEMARK OFFICE
CERTIFICATE OF CORRECTION

PATENT NO.     : 6,048,543
DATED          : April 11, 2000
INVENTOR(S)    : Heinz Schneider It is certified that error appears in the above-identified patent and that said Letters Patent is hereby corrected as shown below:

Title page,
Item [75], Remove Inventor, Ronald G. Thurman, from the patent.
Item [19], "Schneider et al." should be -- Scheider --.

Signed and Sealed this

Fourth Day of September, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 6,048,543
DATED : April 11, 2000
INVENTOR(S) : Heinz Schneider

It is certified that error appears in the above-identified patent and that said Letters Patent is hereby corrected as shown below:

Title page,
Item [75], remove Inventor, Ronald G. Thruman, from the patent.
Item [19], "Schneider et al." should be -- Schneider --.

This certificate supersedes Certificate of Correction issued September 4, 2001

Signed and Sealed this

Twenty-fifth Day of December, 2001

Attest:

JAMES E. ROGAN
Attesting Officer     Director of the United States Patent and Trademark Office